(12) United States Patent
Venon et al.

(10) Patent No.: US 9,734,285 B2
(45) Date of Patent: Aug. 15, 2017

(54) ANATOMY MAP NAVIGATOR SYSTEMS AND METHODS OF USE

(75) Inventors: Medhi Venon, Whitefish Bay, WI (US); Christopher Janicki, Sleepy Hollow, IL (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 610 days.

(21) Appl. No.: 12/783,979

(22) Filed: May 20, 2010

(65) Prior Publication Data

US 2011/0289441 A1   Nov. 24, 2011

(51) Int. Cl.
  *G06F 19/00* (2011.01)
  *G06T 7/00* (2017.01)
  *G06F 3/0484* (2013.01)

(52) U.S. Cl.
  CPC .......... *G06F 19/321* (2013.01); *G06T 7/0016* (2013.01); *G06F 3/04842* (2013.01); *G06T 2200/24* (2013.01); *G06T 2207/30068* (2013.01)

(58) Field of Classification Search
  CPC ...... G06F 3/048; G06F 3/0484; G06F 19/321; G06F 19/3487; G06F 3/04842
  USPC .......................................... 715/771; 382/128
  See application file for complete search history.

(56) References Cited

U.S. PATENT DOCUMENTS

| | | | |
|---|---|---|---|
| 2002/0070970 A1* | 6/2002 | Wood et al. | 345/766 |
| 2003/0199740 A1 | 10/2003 | Iliff | |
| 2006/0280287 A1* | 12/2006 | Esham | A61N 5/1049 378/65 |
| 2007/0122021 A1* | 5/2007 | Zingaretti et al. | 382/132 |
| 2007/0127795 A1* | 6/2007 | Lau et al. | 382/128 |
| 2007/0177780 A1* | 8/2007 | Chui | 382/128 |
| 2007/0245238 A1 | 10/2007 | Fugitt et al. | |
| 2008/0114808 A1 | 5/2008 | Morita et al. | |
| 2008/0118125 A1 | 5/2008 | Mahesh et al. | |
| 2008/0126982 A1* | 5/2008 | Sadikali et al. | 715/810 |
| 2009/0192823 A1* | 7/2009 | Hawkins et al. | 705/3 |
| 2009/0257657 A1* | 10/2009 | Temmermans et al. | 382/195 |
| 2011/0125526 A1* | 5/2011 | Gustafson | G06F 19/321 705/3 |
| 2011/0158487 A1* | 6/2011 | Ohyu et al. | 382/128 |

\* cited by examiner

Primary Examiner — Christopher J Fibbi
(74) Attorney, Agent, or Firm — Hanley, Flight and Zimmerman, LLC

(57) ABSTRACT

Example systems and methods provide anatomy map-based navigation and review of current and historical images and associated evidence. A method for navigating current and reference images and associated evidence includes loading a current image and a reference image for review via a navigator interface based on a time entry selection by a user. One or more markers indicating clinical findings or evidence are registered with at least one of the current image and the reference image. The one or more markers are displayed in conjunction with the current image and the reference image. A synopsis of information associated with a selected marker is provided upon selection of the marker by a user. A user can navigate through image and marker data over time by selecting each of a plurality of time entries to display images and associated markers for user review.

22 Claims, 9 Drawing Sheets

ANATOMY MAP NAVIGATOR SYSTEMS AND METHODS OF USE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

In many screening procedure or post-treatment follow-up procedures, a physician wishes to compare images taken before and during the post procedures recovery. The physician visually compares side by side the images sets to evaluate areas of concern or an evolution of a region of interest. It is a very cumbersome procedure involving lengthy training and a particular setup for all images to perform this side-by-side comparison. When the comparison involves evaluating evolution of an anatomy from information coming from multiple sources, algorithms, or domains related to the same anatomy, the task becomes even more complex, often leading to error and uncertainty in the outcome of the procedure.

BRIEF SUMMARY

Certain embodiments of the present invention provide systems and methods for anatomy map-based navigation and review of current and historical images and associated evidence.

Certain examples provide a computer-implemented method for navigating current and reference images and associated evidence. The method includes loading a current image and a reference image for review via a navigator interface based on a time entry selection by a user. The method also includes registering one or more markers indicating clinical findings or evidence with at least one of the current image and the reference image and associated regional information. The method further includes displaying the one or more markers in conjunction with the current image and the reference image. The method additionally includes providing a synopsis of information associated with a selected marker upon selection of the marker by a user. The method also includes allowing a user to navigate through image and marker data over time by selecting each of a plurality of time entries to display images and associated markers for user review.

Certain examples provide an anatomy map navigation system. The system includes a processor connected to a memory, wherein the processor is programmed to display and facilitate navigation of navigating current and reference images and associated evidence by: loading a current image and a reference image for review via a navigator interface based on a time entry selection by a user; registering one or more markers indicating clinical findings or evidence with at least one of the current image and the reference image; displaying the one or more markers in conjunction with the current image and the reference image; providing a synopsis of information associated with a selected marker upon selection of the marker by a user; and allowing a user to navigate through image and marker data over time by selecting each of a plurality of time entries to display images and associated markers for user review.

Certain examples provide a tangible computer-readable storage medium having a set of instructions stored thereon which, when executed, instruct a processor to implement an anatomy map navigator system. The system includes a navigator interface to include a position for display of a current image, a position for display of a historical image, and a selection of stored image entries. The graphical user interface is to display a current image and a reference image for review based on a stored entry selection by a user. The system also includes a registration engine to register one or more markers indicating clinical findings or evidence with at least one of the current image and the reference image. The registration engine is to provide the one or more markers to the navigator interface to display the one or more markers in conjunction with the current image and associated regional information and the reference image and provide a synopsis of information associated with a selected marker upon selection of the marker by a user. The navigator interface and the registration engine are to allow a user to navigate through image and marker data over time by user selection of each of a plurality of time entries to display images and associated markers for user review.

Figure 1:
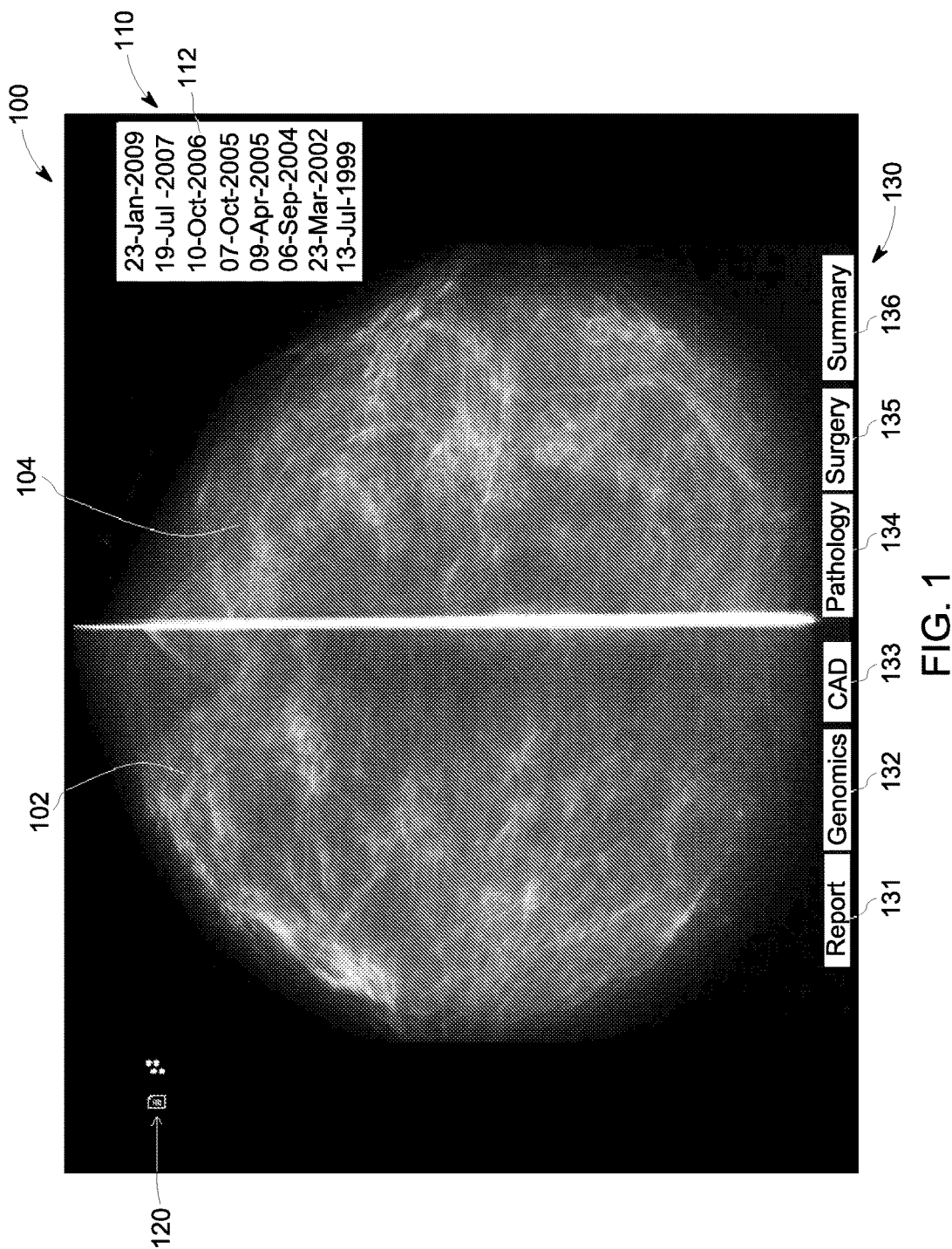
FIG. 1 illustrates an interface and associated workflow to allow a user to navigate through available information to streamline a reading workflow, for example.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain examples provide an anatomy map navigator and associated methods to link and review one or more images from one or more modalities including markers to clinical evidence and annotations associated with one or more regions of interest in the images. Certain examples provide an ability to view, evaluate and analyze changes in the anatomy/region and/or markers over time to facilitate regional trending and comparison of the available data. Certain examples allow highlighting of one or more areas of concern along with image- and date-based navigation of findings and evidence generated with respect to a patient.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, etc. storing the software and/or firmware.

In many screening or post-treatment follow-up procedures, a physician compares images taken before and during the post-procedure recovery. The physician visually compares the images sets side by side to evaluate area(s) of concern, evolution of an anatomy, etc. Performing this side-by-side comparison involves lengthy training for the user, setup for the images, and complex room setup. When the image comparison involves comparing more than two images from the same or different image scanning techniques or technologies, the task becomes more complex, leading to increased possibility for error and uncertainty in the outcome of a procedure.

Certain examples combine information from two or more images linked to the same anatomy from the same or different modality(ies) and register the information in the images and/or corresponding quantitative and/or qualitative data on a "time machine" snap shot image. A current selected image (the latest image or another current image) can become the background image. Changes in the anatomy and/or marker(s), measurements, and/or other evidence are then combined with the reference image(s) to allow comparative, regional trending of the anatomy. Certain examples address the complexity(ies) to present trending information in the image and combine all available historical information to highlight an area of concern and navigate through findings and generated evidence related to the patient.

Combined image information and associated trending can help improve screening procedures to allow early detections of abnormality or to narrow the area to diagnose. Such information and view can also assist in post-treatment follow-up, evaluation of drug treatment and/or other regimen effectiveness, etc. Certain examples can be used in post-evaluation of cancer treatment such as chemotherapy, radiotherapy, and/or combined treatments. Certain examples can also be used during cancer treatment to allow an oncologist to adjust treatments based on patient response, such as by changing dose strategy, shortening treatment, etc. Such adjustment can be important for pediatric cancer treatments, for example.

Additionally, review of images can be extended to a primary care physician to enable the primary care physician and the radiologist and/or referral physician to discuss the findings based on the patient medical image(s). Certain examples can also contribute to improvement of screening of degenerative conditions or pre-conditions.

Certain examples utilize registration, segmentation, and compression techniques between same modality images and/or multi-modalities images to register quantitative and/or qualitative data and/or the images to map the information locally from a reference image. FIG. 1 illustrates an interface 100 and associated workflow to allow a user to navigate through available information to streamline a reading workflow, for example.

To link the images from various studies to a single patient, one or more patient matching algorithms are used. FIGS. 1-7 provide example illustrations of ways in which the information can be presented.

Figure 2:
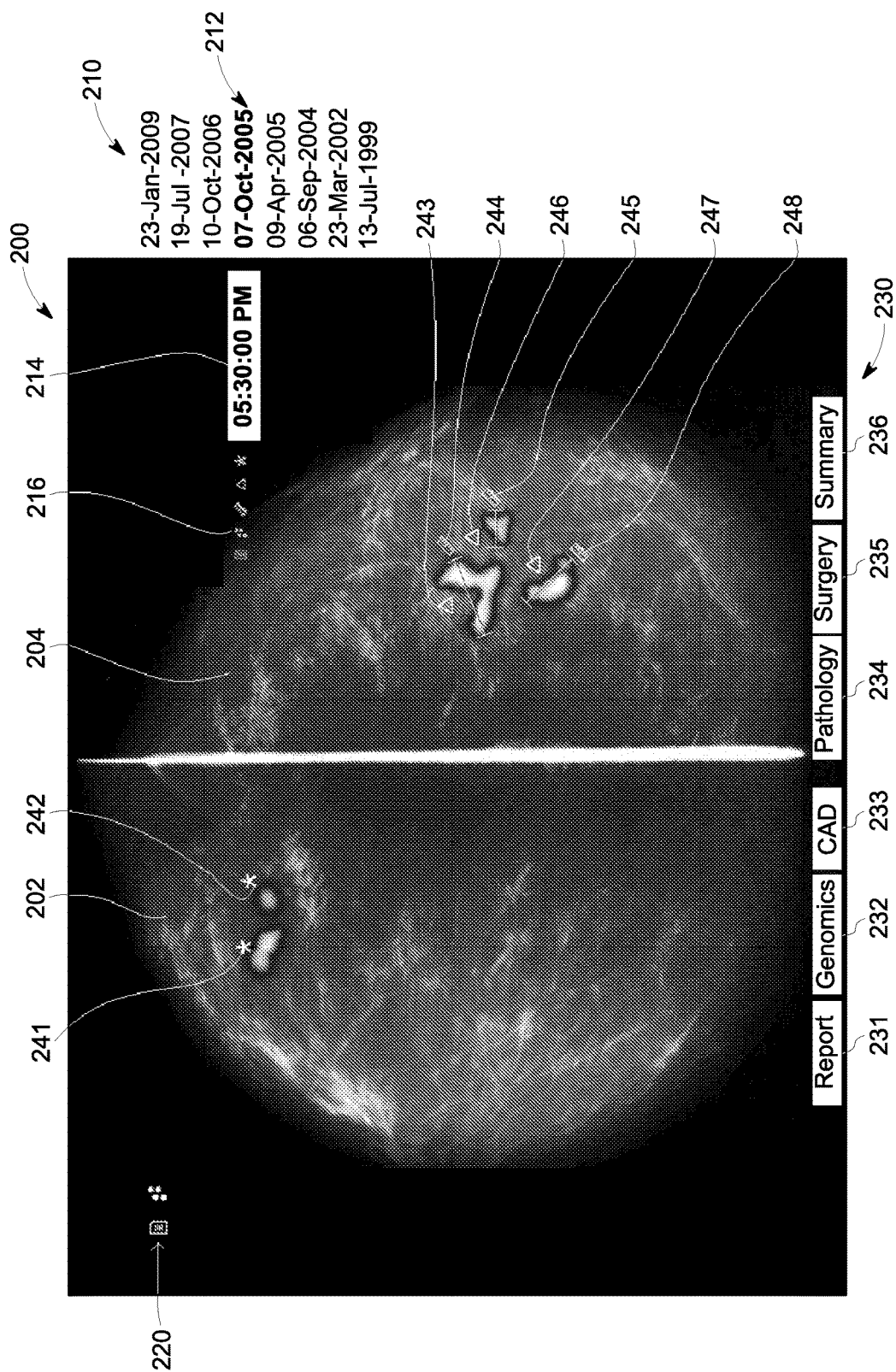
FIGS. 2-7 illustrate example navigation through evidence trends between current and historical images and related information.

FIG. 2 depicts an example anatomy map navigator 200 including information about anatomical changes that are highlighted in the reference image 204. Changes include, but are not limited to, density information, contour, physiological or chemical structure, trending data from computed analysis algorithm, and/or manual annotation of the radiologist. Time markers 210 on the right image 204 allow access to all evidence linked to a specific study. Using time markers 210, information presented on the images 202, 204 can be filtered to display different findings linked to a study in a reference image, which might or might not be the image from which the markers are created.

FIGS. 3-7 illustrate example navigation through evidence trends between current and historical images.

Certain example anatomy navigators not only display radiological information but also map information for surgery, endoscopy, pathology (e.g., related and/or unrelated the pathology), drug prescription (e.g., when the viewer is used to follow the effectiveness of drug prescription in a case (including but not limited to arthroporosis)), etc.

Certain examples provide a powerful workflow to access information related to a patient as well as to summarize a patient anatomy trending snapshot to allow to a radiologist and/or other clinician to focus on area without side-by-side comparison of multiple images.

Certain examples help increase the productivity of radiology by shortening the reading of screening and post-treatment procedures while allowing an overview of anatomy health trending. Certain examples help eliminate many manual steps to determine trending and comparative data during a screening procedure and provide on demand data analysis tailored based on procedure and end-user need/preference. Certain examples provide a viewer to visualize a patient through a "time machine" or time varying dimension to streamline monitoring of a patient evaluation. Certain examples provide systems and methods to link and visualize historical evidence in the form of images and related data for a patient, including a set of controls and guidance for user interactions.

In certain examples, rather than only creating logical associations of data with a patient timeline, information is aggregated on a single overview with an ability to navigate through care actions, health historical record, and evidence generated for the patient. Historical and spatial data can be linked to provide a health overview of the anatomy for a patient. A health map of the anatomy of a body region combined with clinical evidence that is mapped them to corresponding region(s).

FIG. 1 depicts an anatomy map navigator interface 100 including timeline-based navigation of quantitative and qualitative data with associated images. The navigator 100 includes a current image 102 and a reference image 104. The current image 102 can be loaded from an exam being reviewed, while the reference image 104 is provided based on historical data, user preference, image matching, and/or other technique. Current 102 and relevant historical 104 images are opened and registered in the anatomy map navigator 100. Registration techniques provide transformation information to map local or regional information from a past or future exam to the reference image. Information associated and displayed with the images 102, 104 can be navigated using a timeline 110. The timeline navigation control 110 allows a user to select and compare exams by date. The timeline 110 includes one or more date indicators 112 that can be linked to one or more diagnostic markers 120. Markers 120 can be indicators of reports, computed quantitative or qualitative algorithm results, genomics, pathology, surgery reports, treatments reports, etc. The markers 120 appear on the images 102, 104 providing additional relevant information for the clinician. Quick access buttons 130 provide user access to additional functionality such as reports and clinical information. For example, buttons 130 can include a report access button 131, genomics 132, CAD 133, pathology 134, surgery 135, and summary 136.

FIG. 2 depicts an example anatomy map navigator 200 including information regarding anatomical changes that are highlighted in a current image 202 and a reference image 204. Changes include, but are not limited to, density information, trending data from computed analysis algorithm, and/or manual annotation of the radiologist, for example. Time/date indicators 210 allow access to all evidence linked to a specific study corresponding to a particular time entry 212. Using timeline indicators 210, such as time entry 212, information presented on the images 202, 204 can be filtered to display different findings linked to a study in a reference image, which might or might not be the image from which the markers are created. One or more markers 220 are provided in conjunction with the current 202 and reference 204 images. Markers 220 indicate diagnostic and/or clinical information such as CAD, heat maps, measurements, etc., displayed on the image 202 and/or 204 to identify areas of interest and other relevant information.

When a user specifies a particular time indicator 212, such as by rolling over, hovering over, clicking, and/or otherwise selecting the entry 212 with a mouse, trackball, touchpad, touchscreen, holographic input device, voice command, and/or other cursor manipulation device, the study date and time 214 are highlighted. Icons 216 representing available types of markers or indicators are provided for the study in conjunction with the images 202, 204. Selection of an icon 216 provides further information regarding markers of that type displayed in conjunction with the images 202, 204.

Clinical marker(s) 241-248 associated with the image 202, 204 are displayed on the image 202, 204 as icons. Markers 241-248 highlight particular annotations, CAD, heat maps, measurements, etc., on the image 202, 204 for user review. Selection of a marker 241-248, such as by rolling over, hovering over, clicking, and/or otherwise selecting the marker 241-248 with a mouse, trackball, touchpad, touchscreen and/or other cursor manipulation device results in information and/or documentation regarding the marker 241-248 to be displayed for the user. Additionally, selection of a marker type 216 can highlight and/or provide information regarding particular markers 241-248 of the selected type. In some examples, all available markers 241-248 are shown on the images 202, 204, but some markers 241-248 may be highlighted, emphasized, or supported with additional information based on a selected marker type 216. In other examples, by selecting a time marker 212 and a marker type 216, only certain information for a certain exam in time can be filtered and highlighted for the images 202, 204 via the navigator 200. For example, only measurement evidence markers may be highlighted or shown on the images 202, 204 based on a marker or evidence type 216 selection.

Additionally, by selecting one or more functions 230, such as a report 231, genomics 232, CAD 233, pathology 234, surgery 235, or summary 236, information and associated function can be provided to the user in conjunction with the images 202, 204. Such functions 230, used in conjunction with the images 202, 204 and markers 241-248 allow a user to review, analysis, and document anatomical changes in the images 202, 204 over time. Changes such as density, trending, and/or annotation can be reviewed, modified, and/or reported (and/or otherwise exported) by a user, such as a radiologist or reviewing clinician.

Figure 3:
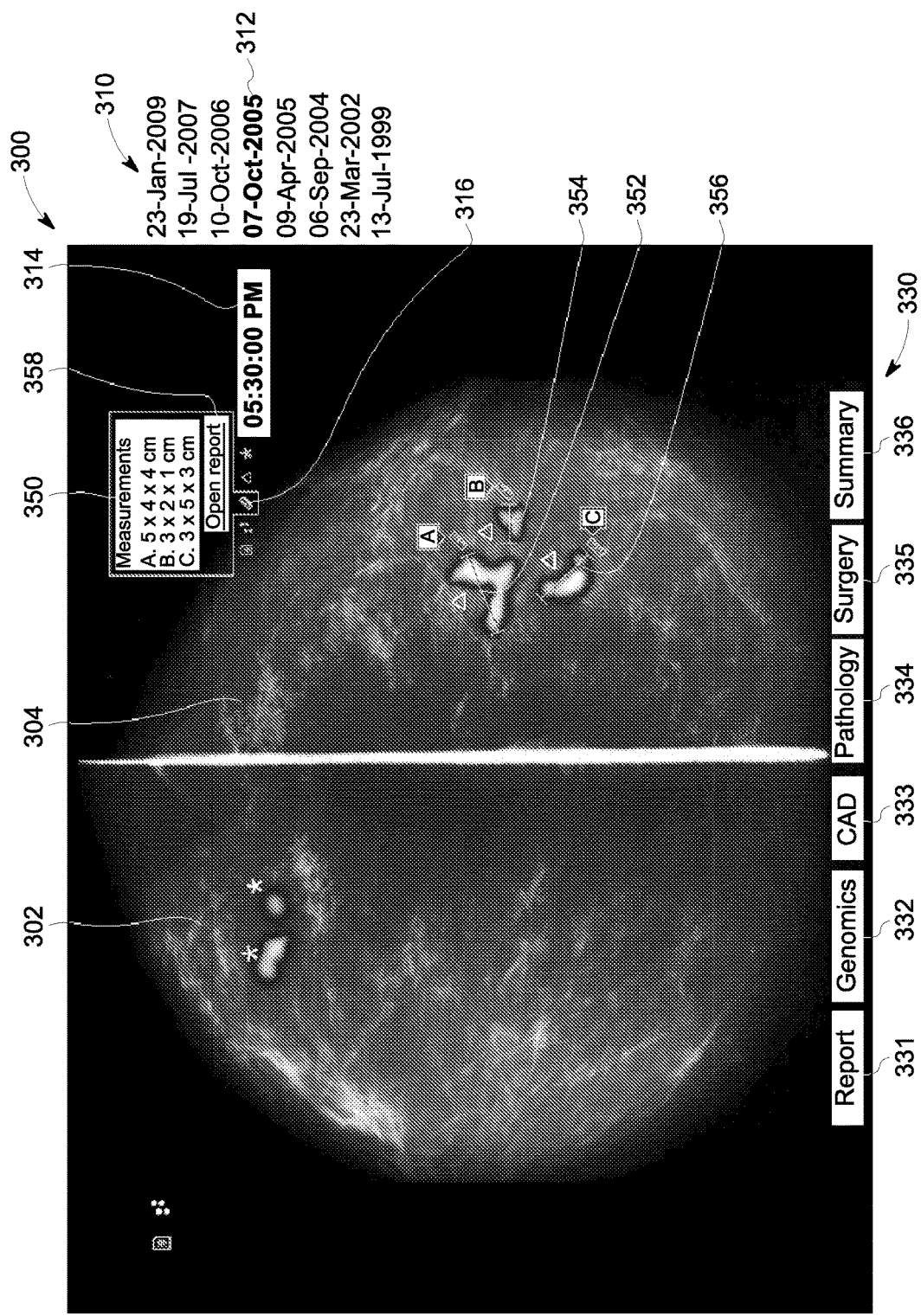

As illustrated, for example, in FIG. 3, an anatomy navigator 300 can provide current 302 and reference or historical 304 images and associated evidence, accessible over time. Using the navigator 300, a user can navigate through clinical and/or other supporting evidence over time between current 302 and historical 304 images. The navigator 300 displays radiological information and can map additional information such as information for surgery, endoscopy, pathology, and/or prescription information to the images 302, 304. The navigator 300 includes one or more time/date indicators 310 corresponding to one or more image studies and associated clinical information, such as measurement, CAD, annotation, and/or other information associated with an image and/or a region of interest within an image. Selecting a time entry 312 provides additional information 314, such as a time of study acquisition, associated with the entry data 312. Selecting a time entry 312, such as by positioning a cursor over the entry 312, clicking on the entry 312, and/or otherwise indicating the entry 312, also provides a set of evidence markers 316 corresponding to the entry 312.

Selection of a particular marker 316 provides additional detail regarding the selected evidence marker type 350. For example, selecting a measurements marker 350 provides information about three labeled measurements for regions of interest annotated on the image 304. Measurements A, B, and C correspond to markers 352, 354, 356 shown on the historical image 304. Selecting the marker type 350 highlights markers 352, 354, 356 with corresponding indicators A, B, C. A user can review the measurements marker 350 information to see dimensions for measurements A, B, C and can open a report 358 including that information.

For example, rolling over a marker 316 in the timeline entry 312 displays a brief synopsis 350 of association clinical information. If multiple, identical markers 352, 354, 356 are found on the image 304, pointers (e.g., A, B, and C) appear near the markers 352, 354, 356 to distinguish each item. Clicking the 'open report' link 358 opens the related full report.

Additionally, by selecting one or more functions 330, such as a report 331, genomics 332, CAD 333, pathology 334, surgery 335, or summary 336, information and associated function can be provided to the user in conjunction with the images 302, 304. Such functions 330, used in conjunction with the images 302, 304 and markers 352, 354, 356 allow a user to review, analysis, and document anatomical changes in the images 302, 304 over time. Changes such as density, trending, and/or annotation can be reviewed, modified, and/or reported (and/or otherwise exported) by a user, such as a radiologist or reviewing clinician.

Figure 4:
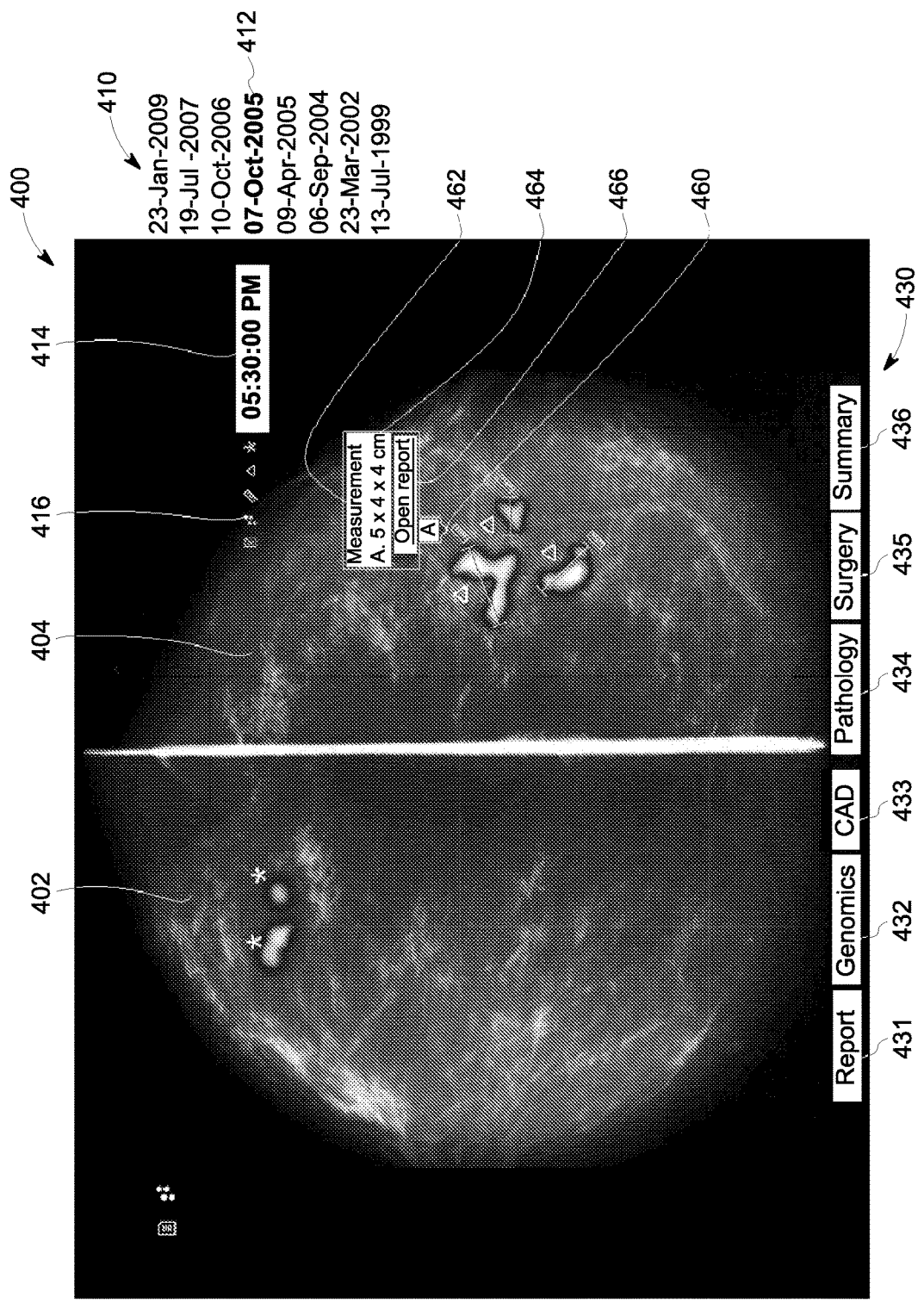

FIG. 4 illustrates another example anatomy navigator 400 facilitating review of current 402 and reference/historical 404 images and associated evidence over time. Using the navigator 400, a user can navigate through clinical and/or other supporting evidence over time between current 402 and historical 404 images. The navigator 400 displays radiological information and can map additional information such as information for surgery, endoscopy, pathology, and/or prescription information to the images 402, 404. The navigator 400 includes one or more time/date indicators 410 corresponding to one or more image studies and associated clinical information, such as measurement, CAD, annotation, and/or other information associated with an image and/or a region of interest within an image. Selecting a time entry 412 provides additional information 414, such as a time of study acquisition, associated with the entry data 412. Selecting a time entry 412, such as by positioning a cursor over the entry 412, clicking on the entry 412, and/or otherwise indicating the entry 412, also provides a set of evidence markers 416 corresponding to the entry 412.

Selecting, such as by rolling, position, or clicking over, a marker 460 on the image 404 displays a synopsis 462 of information associated with the marker 460. For example, selection of the marker 460, which is a measurement marker, provides a synopsis of the measurement information 464 for the region of interest associated with the marker 460. A user can also select to open a report 466 associated with the marker 460 and its measurement 464 that provides additional detail regarding the measurement 464 and/or other feature of the marker 460, for example.

Additionally, by selecting one or more functions 430, such as a report 431, genomics 432, CAD 433, pathology 434, surgery 435, or summary 436, information and associated function can be provided to the user in conjunction with the images 402, 404. Such functions 430, used in conjunction with the images 402, 404 and markers 452, 454, 456 allow a user to review, analysis, and document anatomical changes in the images 402, 404 over time. Changes such as density, trending, and/or annotation can be reviewed, modified, and/or reported (and/or otherwise exported) by a user, such as a radiologist or reviewing clinician.

Figure 5:
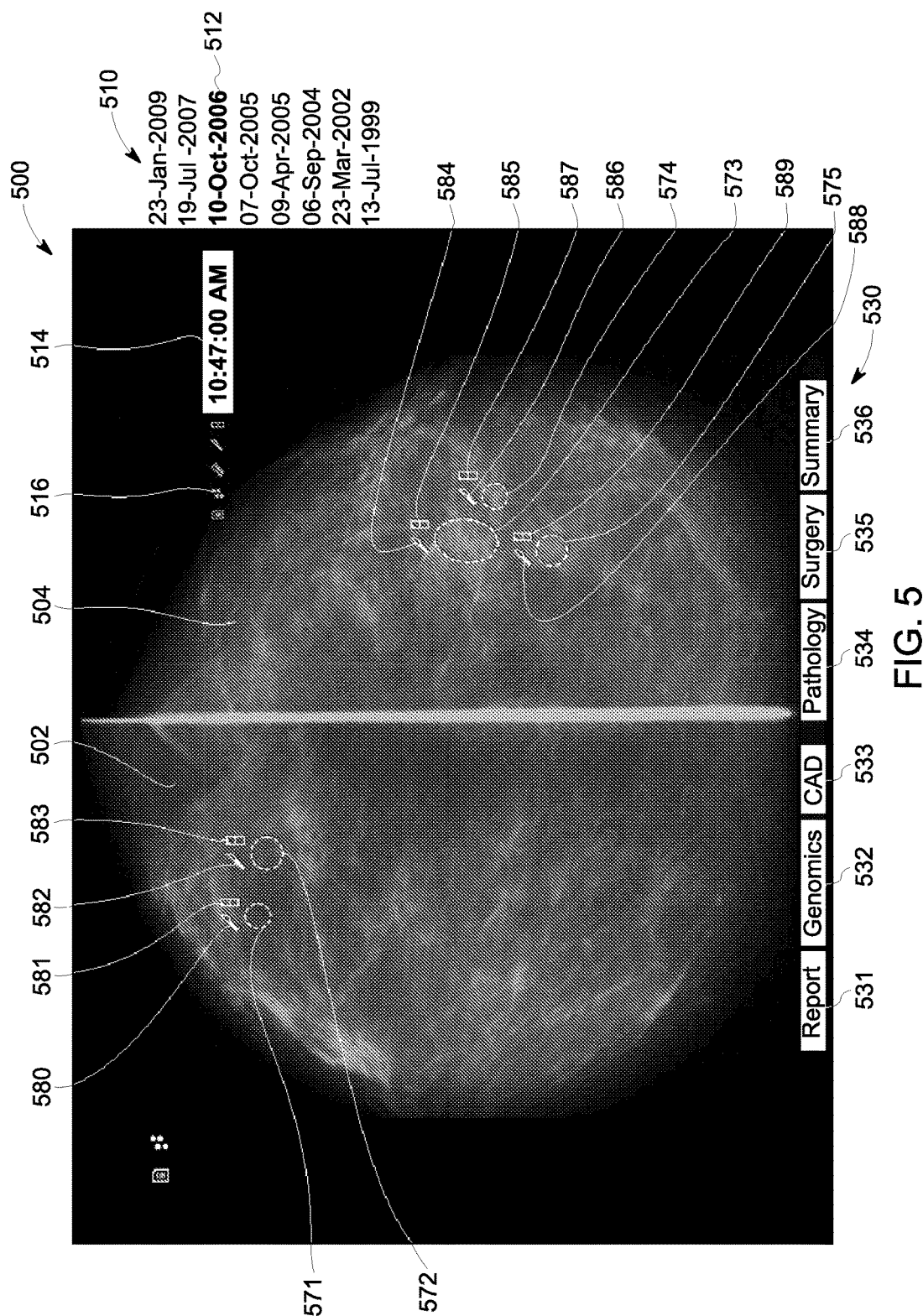

FIG. 5 shows another example anatomy navigator 500 to provide review of current 402 and reference/historical 404 images and associated evidence. Using the navigator 500, a user can navigate through clinical and/or other supporting evidence over time between current 502 and reference 504 images. The navigator 500 displays radiological information and can map additional information such as information for surgery, endoscopy, pathology, and/or prescription information to the images 502, 504. The navigator 500 includes one or more time/date indicators 510 corresponding to one or more image studies and associated clinical information, such as measurement, CAD, annotation, and/or other information associated with an image and/or a region of interest within an image. Selecting a time entry 512 provides additional information 514, such as a time of study acquisition, associated with the entry data 512. Selecting a time entry 512, such as by positioning a cursor over the entry 512, clicking on the entry 512, and/or otherwise indicating the entry 512, also provides a set of evidence markers 516 corresponding to the entry 512.

The navigator 500 of FIG. 5 illustrates a different selected study 512 compared to the selected study 412 of FIG. 4. Based on the study selection 512 of FIG. 5, one or more of the images 502, 504 as well as markers 580-589 displayed with those images 502, 504 has changed. Using the navigator 500, surgical biopsy 580, 582, 584, 586, 588 and pathology 581, 583, 585, 587, 589 markers are shown with respect to regions of interest 571-574. Selecting a marker 580-589, such as by rolling, position, or clicking over, a marker 580-589 on the image 502, 504 displays further information associated with the marker 580-589 and/or region of interest 571-574.

Additionally, by selecting one or more support functions 530, such as a report 531, genomics 532, CAD 533, pathology 534, surgery 535, or summary 536, information and associated function can be provided to the user in conjunction with the images 502, 504. Such functions 530, used in conjunction with the images 502, 504 and markers 580-589 allow a user to review, analysis, and document anatomical changes in the images 502, 504 over time. Changes such as density, trending, and/or annotation can be reviewed, modified, and/or reported (and/or otherwise exported) by a user, such as a radiologist or reviewing clinician.

Figure 6:
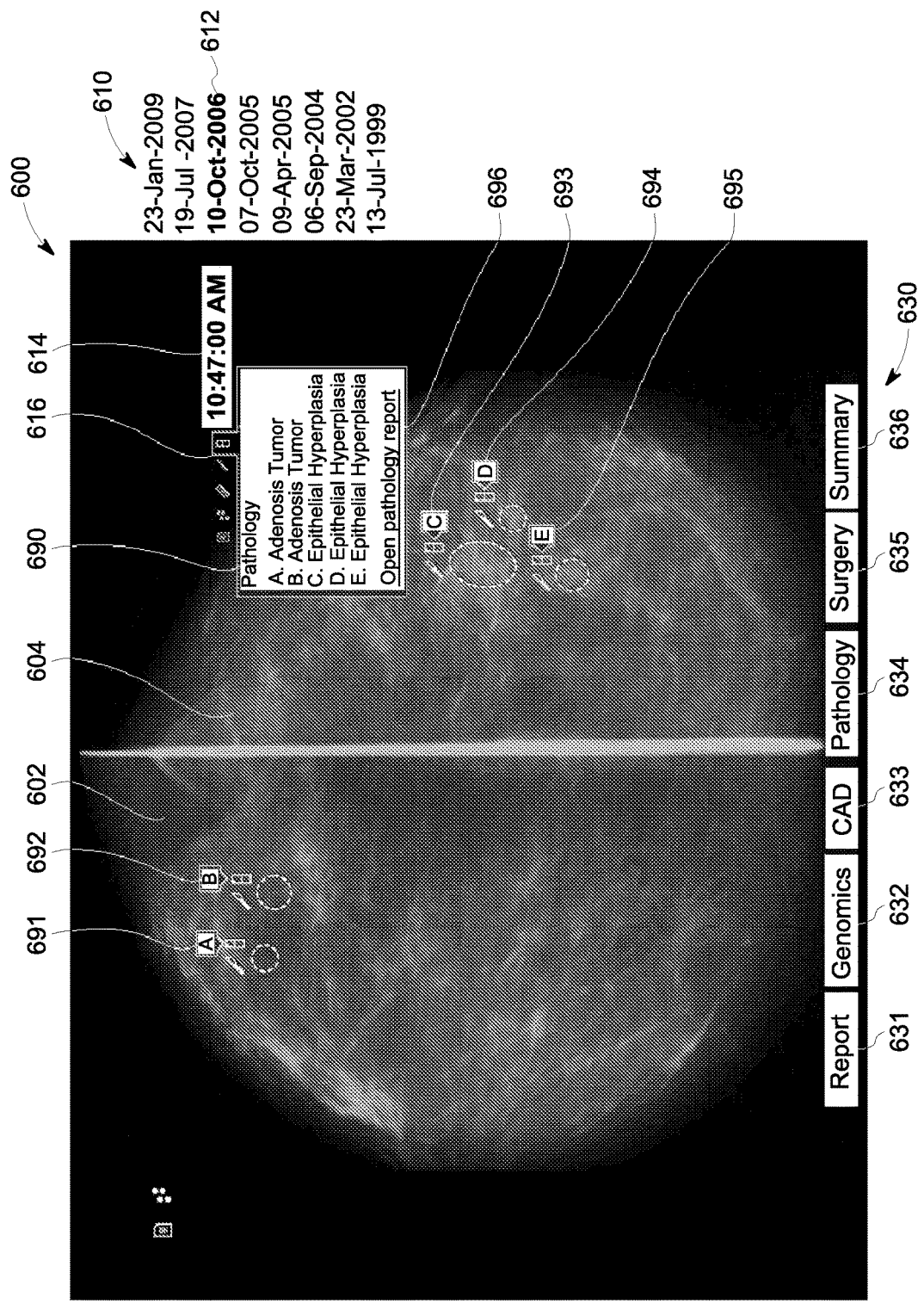

As depicted, for example, in FIG. 6, an anatomy map navigator 600 provides images 602, 604 in association with a selected study 612 from a timeline-based group of studies 610. Additional time information 614 and marker types 616 are provided in conjunction with the selected study 612. A plurality of markers, such as pathology markers 691-695 are provided in conjunction with regions of interest in the images 602, 604.

Selecting, such as by rolling, position, or clicking over, a marker 616 displays a synopsis 690 of information associated with the marker 616. For example, selection of a pathology marker provides a synopsis of pathology findings associated with the image(s) 602, 604. The pathology synopsis provides an indication of pathology findings 691-695 marked on images 602, 604. A user can also select to open a report 696 associated with the marker 616 to open a full pathology report.

Additionally, by selecting one or more support functions 630, such as a report 631, genomics 632, CAD 633, pathology 634, surgery 635, or summary 636, information and associated function can be provided to the user in conjunction with the images 602, 604. Such functions 630, used in conjunction with the images 602, 604 and markers 691-695 allow a user to review, analysis, and document anatomical changes in the images 602, 604 over time. Changes such as density, trending, and/or annotation can be reviewed, modified, and/or reported (and/or otherwise exported) by a user, such as a radiologist or reviewing clinician.

Figure 7:
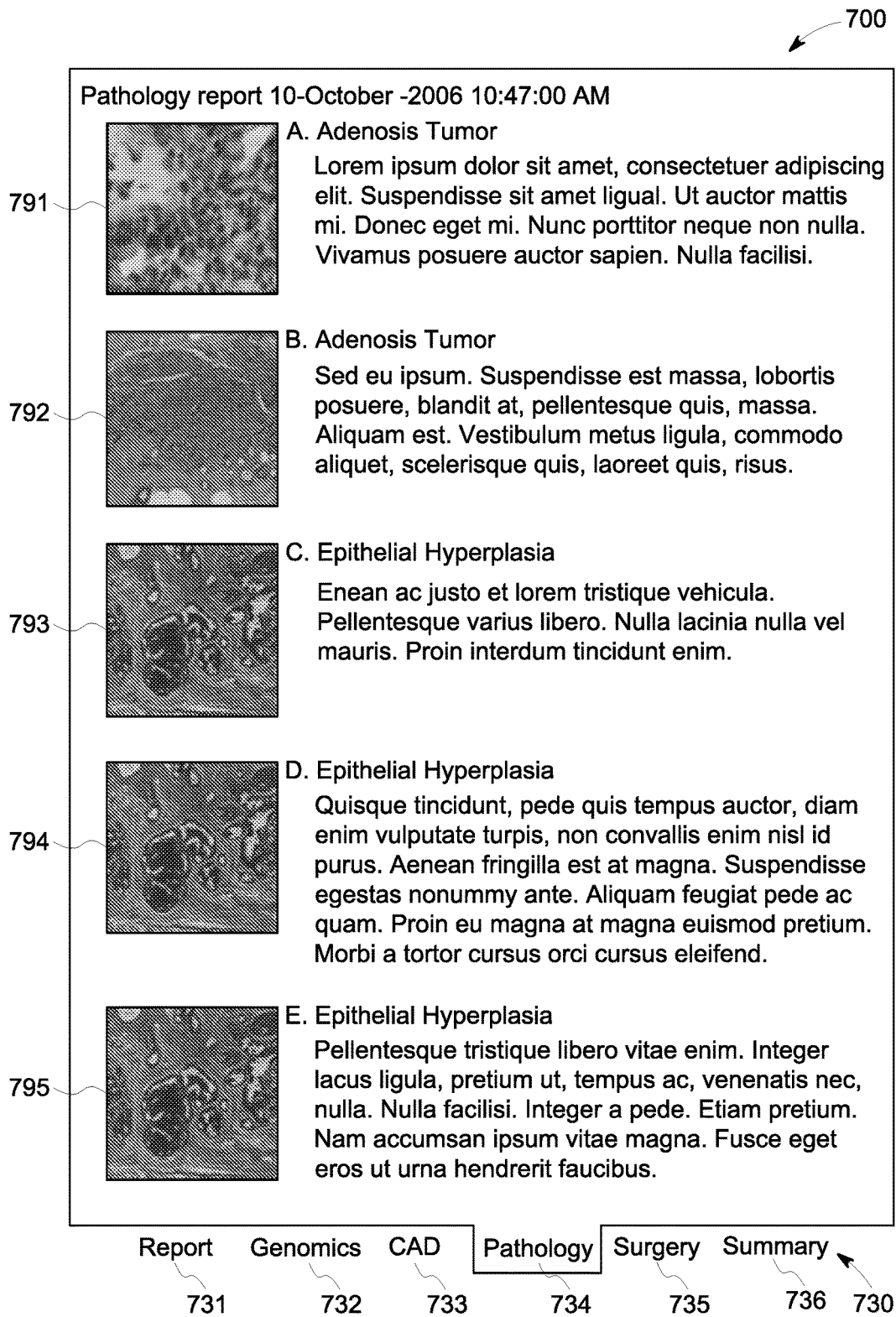

As discussed above, selecting a reporting and/or decision support option 130, 230, 330, 358, 430, 466, 530, 630, 696 provides access to more detailed information regarding one or more types of findings, such as measurement, biopsy, pathology, genomics, CAD, etc. FIG. 7 illustrates an example in which link 696 from navigator 600 of FIG. 6 is selected to open a full pathology report 734. The pathology report 734 includes pathology information 791-795 corresponding to each marker 691-695 (markers A, B, C, D, and E) shown in FIG. 6. The detailed report 734 can be opened by clicking on or otherwise selecting the 'open report' link in the previously discussed preview window or by clicking on or otherwise selecting the button or indicator 731-736 at the bottom of the screen. Underlying facts and details regarding the particular medical evidence can be examined via the detailed report.

While the examples show two images displayed side by side, one or more of the navigator interfaces discussed above can be modified to display more than two images in side by side, tiled, and/or other configurations.

Although many examples are described above with respect to historical images. Reference images can include future or predictive information determined based on one or more predictive algorithms and/or tracking techniques using model based or statistical approaches, for example.

In certain examples, a mobile device allows a user to display and interact with medical content stored on one or more clinical systems via the mobile or handheld device. A user can manipulate content, access different content, and collaborate with other users to analyze and report on exams and other medical content. In some examples, a change in device orientation and/or position results in a change in device mode and set of available tools without closing or losing the patient context and previous screen(s) of patient information. Images can be manipulated, annotated, highlighted, and measured via the device. Enterprise functionality and real-time collaboration are provided such that the user can collaborate on a document in real time with other users as well as access content from systems such as a RIS, PACS, EMR, etc., and make changes via the handheld device.

The handheld device can display and interact with medical content via a plurality of modes. Each mode includes different content and associated tools. Each of the plurality of modes is accessible based on a change in orientation and/or position of the device while maintaining a patient context across modes. The handheld device also includes medical content analysis capability for display, manipulation, and annotation of medical content and real-time sharing of the content for user collaboration using multi-touch control by the user. The handheld device communicates with one or more clinical systems to access and modify information from the one or more clinical systems in substantially real-time.

The handheld device can be used to facilitate user workflow. For example, the handheld device uses an accelerometer and/or global positioning sensor and/or other positional/motion indicator to allow a user to navigate through different screens of patient content and functionality. The handheld device removes the requirement of using a user interface control to select between different screens. For example, multi-touch capability is provided to manipulate and modify content. Using multi-touch, a user can draw shapes and annotate to generate measurements, highlight abnormal structure, and/or add textual comments to an image, for example. Via the handheld device, a user can input and/or manipulate without adding external input devices. The position and motion sensor(s) are used to manipulate the navigation direction in the colonoscopy and/or the navigation speed, for example.

In certain examples, the handheld device provides enhance resetability for the user. For example, the device can undo, erase, and/or reset end user changes to default setting by tracking a device's position and/or orientation and responding to changes to the position/orientation. The device can undo and restart without additional user interface control input. The device can adjust a threshold parameter through user feedback, for example (e.g., a current setting may be too sensitive to normal movement of the device when carried or held by a user).

Certain examples integrate enterprise functions into a mobile device. For example, functionality such as a directory, calendar, geographic location, phone services, text message, email, etc., can be provided via the mobile device. Clinical information from various sources such as PACS, HIS, RIS, EMR, etc., can be provided via the mobile device. The mobile device interface can facilitate real-time collaboration with other end users. Information sharing and recording can be facilitated using multiple media services in real-time or substantially real-time, for example. The mobile device allows the user to focus on patient information and analysis while collaborating with one or more end users without switching or leaving the clinical context being reviewed, as well as exchanging medical data without losing the current state of the clinical context, for example. The mobile device provides a unified communication/collaboration point that can query and access information throughout different information systems, for example.

Certain examples facilitate user authentication via the mobile device. For example, the mobile device can authenticate a user's access to sensitive and/or private information. In certain embodiments, user authentication at the mobile device does not require the user to enter an identifier and password. Instead, the user is known, and the mobile device verifies if the current user is authorized for the particular content/application. Authentication is based on a unique identification number for the device, a connectivity parameter, and a PIN number for the user to enter, for example.

In some examples, a user is provided with an ability to share findings and a walk-through of the findings using a smartphone (e.g., BlackBerry™, iPhone™, etc.) or other handheld device such as an iPod™ or iPad™. Doctors can discuss the findings with the patient by replaying the reading, for example. In some examples, a user is provided with an ability to have a second opinion on the findings from a specialist and/or another radiologist without being in proximity to a workstation. The reading radiologist can contact a specialist for a second opinion and to provide feedback (e.g., commentaries and/or annotations) on the same procedures. The first physician can review and acknowledge or edit (e.g., a document review with tracking changes) the second radiologist's annotation.

Figure 8:
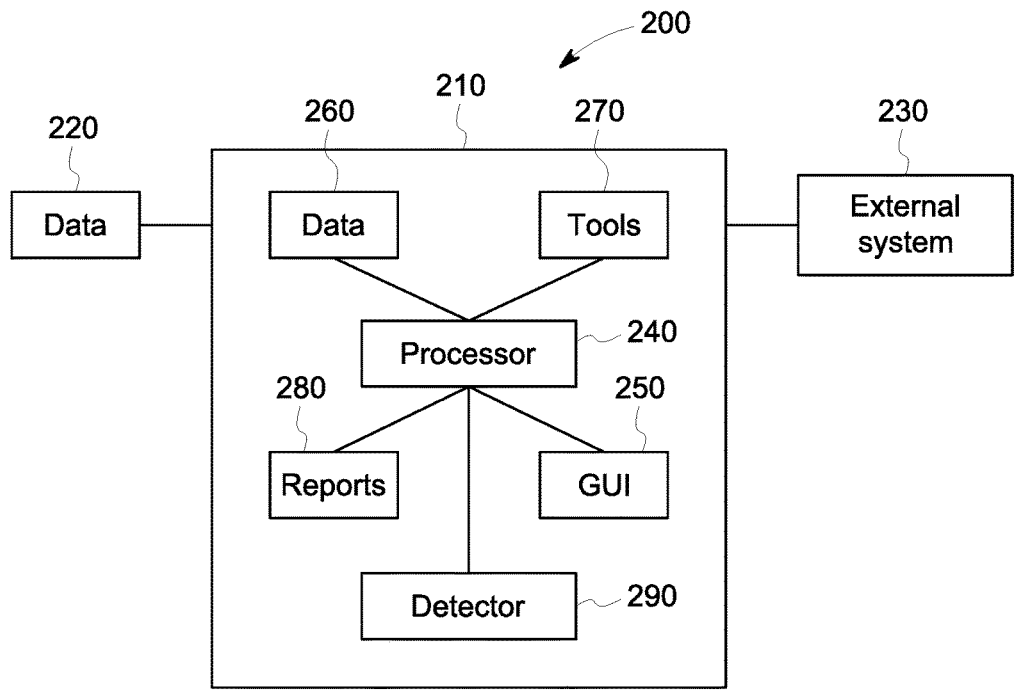
FIG. 8 depicts an example mobile system usable with anatomy map navigator systems and methods.

FIG. 8 depicts an example navigator system 800 including a device 810, an external data source 820, and an external system 830. In some examples, the external data source 820 and external system 830 can be implemented in a single system. In some examples, a plurality of data sources 820 and/or external systems 830 can communicate with the device 810. In some examples, a plurality of devices 810 can communicate with one or more data sources 820 and/or external systems 830. The device 810 can be a mobile device, such as an iPhone™, iPod™, iPad™, BlackBerry™, etc., or a computing workstation or other traditional computing device, for example.

The data source 820 can provide images and/or other data to the navigator device 810. In some examples, the data source 820 can also receive results, reports, and/or other information from the navigator device 810. The external system 830 can receive results, reports, and/or other information from the navigator device 810, for example. In some examples, the external system 830 can also provide images and/or other data to the navigator device 810. The data source 820 and/or external system 830 can be implemented using a system such as a PACS, RIS, HIS, CVIS, EMR, archive, data warehouse, imaging modality (e.g., x-ray, CT, MR, ultrasound, nuclear imaging, etc.).

As discussed above, in some examples, the navigator device 810 can be implemented using a smart phone (e.g., BlackBerry™, iPhone™, iPad™, etc.), Mobile Internet device (MID), personal digital assistant, cellular phone, handheld computer, etc. The navigator device 810 includes a processor 840 retrieving data, executing functionality, and storing data at the mobile device 810, data source 820, and/or external system 830. The processor 840 drives a graphical user interface (GUI) 850 providing information and functionality to a user and receiving user input to control the device 810, edit information, etc. The GUI 850 can include a touch pad/screen integrated with and/or attached to the device 810, for example. The device 810 includes one or more internal memories and/or other data stores including data 860 and tools 870. Data storage can include any of a variety of internal and/or external memory, disk, Bluetooth remote storage communicating with the device 810, etc. Using user input received via the GUI 850 as well as information and/or functionality from the data 860 and/or tools 870, the processor can generate one or more reports 880 related to activity at the device 810, for example. The processor 840, GUI 850, data 260, and tools 270 can be used to implement and provide a navigator interface and registration engine to provide anatomy map navigation as described herein. A detector 890, such as an accelerometer, position encoder (e.g., absolute, incremental, optical, analog, digital, etc.), global positioning sensor, and/or other sensor, etc., can be used to detect motion of the device 810 (e.g., shaking, rotating or twisting, left/right turn, forward/backward motion, etc.). Detected motion can be used to affect operation and/or outcomes at the device 810. The processor 840 can include and/or communicate with a communication interface component to query, retrieve, and/or transmit data to and/or from a remote device, for example.

In operation, for example, the device 810 requests (and/or receives via a push rather than pull model) one or more data sets (e.g., images and optionally associated data such as annotations including but not limited to structured reporting) from the data source 820 for user (e.g., radiologist) review. The data 860 and tools 870 on the navigator device 810 facilitate user navigation, annotation, editing, and/or reporting (e.g., report(s) 880) via the device 810. Motion detected by the detector 890 facilitates user navigation through current and historic and/or other reference images. In some examples, a default translation between detected device 810 movement is provided. In some examples, a user and/or application can custom one or movement translations. Output (e.g., a report 880) can be transmitted to the external system 830 via a communication interface on the device 810.

Mobile devices (including but not limited to a smart phone (e.g., BlackBerry™, iPhone™, iPad™, etc.), laptop, personal digital assistant, cellular phone, handheld computer, etc.) follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages a multi-touch input device such as but not limited to; Personal Identification Number, Keyword, Drawing/Writing a signature (including but not limited to; a textual drawing, drawing a symbol, drawing a pattern, performing a gesture, etc.), etc., to provide a quick, natural, and intuitive method of authentication. Feedback can be provided to the user regarding successful/unsuccessful authentication through display of animation effects on a mobile device user interface. For example, the device can produce a shaking of the screen when user authentication fails. Security standards, virtual private network access, encryption, etc., can be used to maintain a secure connection.

For example, an end user launches a secure application (including but not limited to a clinical application requiring a degree of security). The application reads the unique identifying features of the device and perform an authentication "hand-shake" with the server or data-providing system. This process is automated with no user input or interaction required. After the device has been authenticated, the user is presented with an application/user level authentication screen (including but not limited to a personal identification number (PIN), password/passcode, gesture, etc.) to identify to the application that the user is indeed a valid user. This feature functions as a method to provide device level security as well as an ability to lock the device (e.g., if the user wishes to temporary lock the device but not logout/shutdown the application), for example.

In certain embodiments, mobile devices, such as but not limited to smart phones, ultra mobile and compact notebook computers, personal digital assistants, etc., offer many applications aside from phone functions. Certain embodiments allow clinical end users to enhance their collaboration with their colleagues, patients, and hospital enterprise via the mobile device.

By integrating enterprise functions for mobile devices, such as but not limited to a directory, calendar, geographic location, phone services, text messages, email services, etc., with clinical information from various clinical sources, such as but not limited to PACS, HIS, RIS, etc., end users can access patient centric information and enable real-time or substantially real-time collaboration with other end users to collaborate on a specific patient case. The collaboration allows information sharing and recording using multiple media services in real-time or substantially real-time.

Collaboration leverages global positioning system, multi-touch capability, high resolution displays, etc., in mobile devices within small form factors, for example. Using the mobile device, the end user can focus on patient information analysis while collaborating with one or many other end users without switching or leaving the clinical context being reviewed. It allows exchanging medical data without losing the current state of the clinical context. It also leverages all the multi-media features of a device from healthcare applications. For example, clinical and non-clinical information can be provided to aid a clinical user, such as a physician, nurse, technologist, administrator, etc., in patient care and workflow decisions. The mobile device provides the user with an ability to locate and contact another user (including but not limited to a patient, referring physician, surgeon, pharmacy, emergency patient contact, etc.). The mobile device provides an ability to locate and provide directions with a map to an address of another user, department, or institution (including but not limited to a home address, business address, drug store, hospital clinic, hospital remote facility, specialized clinical facility, etc.). Using a contact address and current location determined by a built-in global positioning feature, a map and guide route can be generated to the destination. This feature also allows relatively accurate time estimates for travel to reach a destination. The mobile device provides an ability to locate and contact another user involved in a patient's care by navigating a user interface that provides contact information of other users involved in the patient's care. Communication is then initiated (including but not limited to by phone, SMS, text messaging, email services, etc.) to collaborate on a patient's exam/case/care. Other users can be included as needed by using the interface (including but not limited to a multi-touch user interface) to search through a contact list (including but not limited to a local contact list, enterprise contact list, clinical context contact list, etc.). Clinical information can then be conveyed to collaborators through a variety of communication methods (including but not limited to phone, SMS, text messaging, email services, etc.) and added to the patient's care record (including but not limited to Clinical Report, Audit Tracking, etc.). Navigation through this information is provided by a user interface that accepts multi-touch user input, for example.

Figure 9:
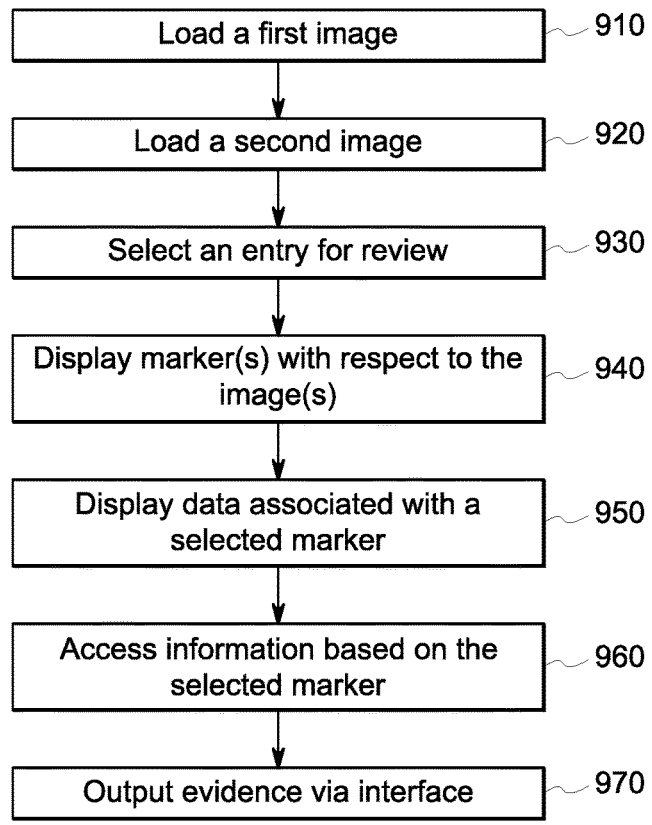
FIG. 9 illustrates a flow diagram for an example method for image navigation.

FIG. 9 illustrates a flow diagram for an example method 900 for image navigation. FIG. 9 depicts an example flow diagram representative of processes that may be implemented using, for example, computer readable instructions that may be used to facilitate reviewing of anatomical images and related clinical evidence. The example processes of FIG. 9 may be performed using a processor, a controller and/or any other suitable processing device. For example, the example processes of FIG. 9 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 9 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 9 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 9 may be implemented manually or as any combination(s) of any of the foregoing techniques, for example, any combination of firmware, software, discrete logic and/or hardware. Further, although the example processes of FIG. 9 are described with reference to the flow diagram of FIG. 9, other methods of implementing the processes of FIG. 9 may be employed. For example, the order of execution of the blocks may be changed, and/or some of the blocks described may be changed, eliminated, sub-divided, or combined. Additionally, any or all of the example processes of FIG. 9 may be performed sequentially and/or in parallel by, for example, separate processing threads, processors, devices, discrete logic, circuits, etc.

Referring to FIG. 9, at 910, a first image of a user anatomy is loaded. The first image can be an image from a current or newly obtained exam or another selected image, for example. The first image can be automatically loaded based on one or more defined rules and/or user preferences, for example. At 920, a second image is loaded. The second image can be a reference and/or other historical image of the anatomy depicted in the first image. The second image can be retrieved from a prior study of the same patient, for example. In some examples, the first and second images are associated with the same anatomy but are obtained using different modalities. The images can be initially presented as snap shot images accessible via a timeline and/or selectable series of study entries, for example. Information, such as quantitative and/or qualitative evidence, associated with the images can be registered to the images and displayed in conjunction with the first and second images via a navigator interface.

At 930, an exam date and/or other entry is selected via a timeline navigator. For example, a particular study or exam date is selected from a listing of available dates in the timeline navigator. At 940, one or more markers indicating clinical and/or other data are displayed with respect to the current and/or historical images based on the study selection. In some examples, the second or historical image changes in the navigator display based on the entry selection, which retrieves another study image for review. Alternatively or in addition, information, such as quantitative and/or qualitative clinical evidence, associated with the image(s) changes in response to the entry selection. Changes in the anatomy and/or associated markers, measurements, and/or other evidence is combined with the current and reference images to facilitate compared regional trending of the anatomy.

At 950, data associated with a selected marker is displayed. For example, reports, CAD, pathology, genomics, surgical information, summary, etc., can be indicated generally in association with an image and/or particularly in association with a region of interest in an image. At 960, information is accessed based on a selected marker. For example, by selecting a marker on an image, such as by rollover, clicking on, and/or otherwise choosing a marker with a cursor and cursor manipulation device or touchscreen, information associated with that marker can be displayed on the interface in conjunction with the image(s). In some examples, an initial selection of a marker provides a synopsis of information associated with that marker. A further selection of the marker and/or an option within the synopsis can provide further and/or more detailed information, such as opening a report. In some examples, information associated with a marker can be modified by a user via the interface. For example, a user can add further comments regarding findings via the interface. As another example, a user can add additional markers to an image via the interface.

At 970, a report and/or other associated evidence can be output via the interface. For example, a report and/or other clinical evidence can be printed, routed to another user, and/or saved in data storage from the navigator interface. As another example, updates and/or changes to a report and/or other information can be saved to a data storage, etc. In some examples, collaboration between clinicians can be facilitated using the images and associated evidence. For example, a clinician at a viewing workstation and a clinician using a mobile device, such as an iPad™ or other tablet-based computing device, can collaborate regarding images and associated content via the navigator interface.

As described herein, the method 900 can be implemented using the mobile device in one or more combinations of hardware, software, and/or firmware, for example. The method 900 can operate with the mobile device in conjunction with one or more external systems (e.g., data sources, healthcare information systems (RIS, PACS, CVIS, HIS, etc.), archives, imaging modalities, etc.). One or more components of the method 900 can be reordered, eliminated, and/or repeated based on a particular implementation, for example.

Figure 10:
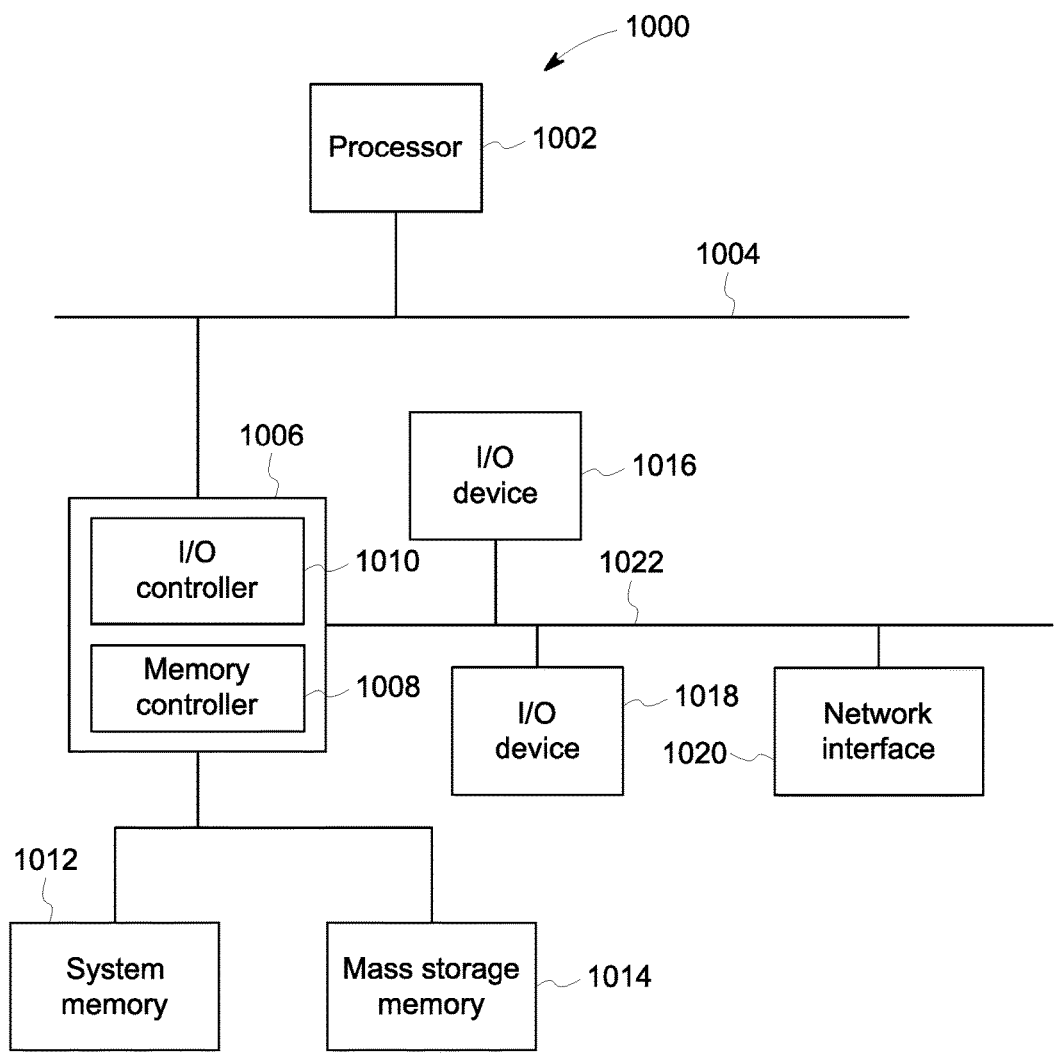
FIG. 10 is a block diagram of an example processor system that can be used to implement the apparatus and methods described herein.

FIG. 10 is a block diagram of an example processor system 1010 that can be used to implement the apparatus and methods described herein. As shown in FIG. 10, the processor system 1010 includes a processor 1012 that is coupled to an interconnection bus 1014. The processor 1012 may be any suitable processor, processing unit or microprocessor. Although not shown in FIG. 10, the system 1010 can be a multi-processor system and, thus, can include one or more additional processors that are identical or similar to the processor 1012 and that are communicatively coupled to the interconnection bus 1014.

The processor 1012 of FIG. 10 is coupled to a chipset 1018, which includes a memory controller 1020 and an input/output (I/O) controller 1022. As is well known, a chipset typically provides I/O and memory management functions as well as a plurality of general purpose and/or special purpose registers, timers, etc. that are accessible or used by one or more processors coupled to the chipset 1018. The memory controller 1020 performs functions that enable the processor 1012 (or processors if there are multiple processors) to access a system memory 1024 and a mass storage memory 1025.

The system memory 1024 can include any desired type of volatile and/or nonvolatile memory such as, for example, static random access memory (SRAM), dynamic random access memory (DRAM), flash memory, read-only memory (ROM), etc. The mass storage memory 1025 can include any desired type of mass storage device including hard disk drives, optical drives, tape storage devices, etc.

The I/O controller 1022 performs functions that enable the processor 1012 to communicate with peripheral input/output (I/O) devices 1026 and 1028 and a network interface 1030 via an I/O bus 1032. The I/O devices 1026 and 1028 can be any desired type of I/O device such as, for example, a keyboard, a video display or monitor, a mouse, etc. The network interface 1030 may be, for example, an Ethernet device, an asynchronous transfer mode (ATM) device, an 802.11 device, a DSL modem, a cable modem, a cellular modem, etc. that enables the processor system 1010 to communicate with another processor system.

While the memory controller 1020 and the I/O controller 1022 are depicted in FIG. 10 as separate blocks within the chipset 1018, the functions performed by these blocks may be integrated within a single semiconductor circuit or may be implemented using two or more separate integrated circuits.

Thus, certain examples provide an anatomy map navigator systems and associated methods. Certain examples provide a technical effect to link and review one or more images from one or more modalities including markers to clinical evidence and annotations associated with one or more regions of interest in the images and provide an ability to view and analyze changes in the anatomy and/or markers over time to facilitate regional trending and comparison of the available data. Certain examples use image registration and segmentation techniques along with patient matching algorithms to provide single- and/or multi-modality images with registered quantitative, qualitative, and/or other clinical evidence for a patient over time to allow a user to navigate through the information in a streamlined reading workflow. Certain examples provide a viewer to visualize a patient through a timeline or "time machine" dimension to streamline monitoring and patient evaluation.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN), a wide area network (WAN), a wireless network, a cellular phone network, etc., that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for navigating current and reference images and associated evidence comprising:
   loading a current image for review via a first area of a navigator interface, the navigator interface providing a single overview to facilitate navigation through care actions, a health historical record and clinical evidence generated for a patient;
   registering one or more markers indicating clinical evidence and annotations with the current image;
   displaying, via the navigator interface, the one or more markers on the current image;
   displaying, via the navigator interface, a set of available marker types corresponding to a type of each registered marker displayed on the current image;
   extracting snap shot data from a plurality of historical reference images based on a selection of a time entry on an interactive timeline displayed via a second area of the navigator interface;
   providing a synopsis and trend of clinical information associated with a selected marker type based on the snap shot data in a third area of the navigator interface, the third area overlaid on the current image in the first area upon selection, by a user, of the selected marker type from the set of available marker types displayed via the navigator interface;
   providing additional information associated with a selected marker upon selection, by the user, of the selected marker on the current image; and
   allowing the user to navigate through image and marker data over time by selecting each of a plurality of time entries provided via the interactive timeline within the single overview of the navigation interface to display images and associated markers for user review,
   wherein the one or more markers on the current image are visible on the current image through the third area overlaid on the current image, and wherein one or more markers corresponding to the selected marker type are highlighted on the current image when included in the synopsis.

2. The method of claim 1, wherein selection comprises at least one of positioning a cursor over the marker, clicking on marker using a cursor control device, and touching the marker using a touch screen.

3. The method of claim 1, wherein the plurality of time entries comprise a plurality of patient exams.

4. The method of claim 1, wherein one or more of the markers highlight anatomical changes over time.

5. The method of claim 4, wherein anatomical changes include at least one of density information, computer aided diagnosis trending data, and radiologist analysis.

6. The method of claim 1, wherein providing comprises providing a synopsis for both a type of marker and a specific selected marker.

7. The method of claim 6, wherein a type of marker comprises at least one of a report, computer aided diagnosis, genomics, pathology, and surgical biopsy.

8. The method of claim 1, further comprising facilitating user navigation through clinical evidence by selecting a time entry for a study among a plurality of study entries and then selecting a marker type from among a plurality of marker types to display associated images in conjunction with markers and associated information on the images for trending and comparative data review.

9. The method of claim 8, wherein image and marker information is customized based on procedure and user preference.

10. The method of claim 1, further comprising opening a report corresponding to the selected marker for user review.

11. The method of claim 1, wherein registering further comprises registering one or more markers indicating clinical findings or evidence with at least one of the current image and the reference image using image registration, image segmentation, and patient matching.

12. The method of claim 1, wherein the synopsis of clinical information includes at least one of a synopsis of measurement information and a synopsis of pathology findings associated with the selected market.

13. An anatomy map navigation system comprising:
   a processor connected to a memory, wherein the processor is programmed to display and facilitate navigation of navigating current and reference images and associated evidence by:
   loading a current image for review via a first area of a navigator interface, the navigator interface providing a single overview to facilitate navigation through care actions, a health historical record and clinical evidence generated for a patient;
   registering one or more markers indicating clinical evidence and annotations with the current image;
   displaying, via the navigator interface, the one or more markers on the current image;
   displaying, via the navigator interface, a set of available marker types corresponding to a type of each registered marker displayed on the current image;
   extracting snap shot data from a plurality of historical reference images based on a selection of a time entry on an interactive timeline displayed via a second area of the navigator interface;
   providing a synopsis and trend of clinical information associated with a selected marker type based on the snap shot data in a third area of the navigator interface, the third area overlaid on the current image in the first area upon selection, by a user, of the selected marker type from the set of available marker types displayed via the navigator interface;

providing additional information associated with a selected marker upon selection, by the user, of the selected marker on the current image; and allowing the user to navigate through image and marker data over time by selecting each of a plurality of time entries provided via the interactive timeline within the single overview of the navigation interface to display images and associated markers for user review, wherein the one or more markers on the current image are visible on the current image through the third area overlaid on the current image, and wherein one or more markers corresponding to the selected marker type are highlighted on the current image when included in the synopsis.

14. The system of claim 13, wherein one or more of the markers highlight anatomical changes over time.

15. The system of claim 14, wherein anatomical changes include at least one of density information, computer aided diagnosis trending data, and radiologist analysis.

16. The system of claim 13, wherein providing comprises providing a synopsis for both a type of marker and a specific selected marker.

17. The system of claim 16, wherein a type of marker comprises at least one of a report, computer aided diagnosis, genomics, pathology, and surgical biopsy.

18. The system of claim 13, further comprising facilitating user navigation through clinical evidence by selecting a time entry for a study among a plurality of study entries and then selecting a marker type from among a plurality of marker types to display associated images in conjunction with markers and associated information on the images for trending and comparative data review.

19. The system of claim 18, wherein image and marker information is customized based on procedure and user preference.

20. The system of claim 13, wherein one or more markers includes predictive information determined based on one or more predictive algorithms and tracking techniques using at least one of model based and statistical analysis.

21. A non-transitory computer-readable storage medium having a set of instructions stored thereon which, when executed, instruct a processor to implement an anatomy map navigator system, the system comprising:

a navigator interface to include a position for display of a current image and a selection of stored image entries, the graphical user interface to display, in a first area, a current image for review based on a stored entry selection by a user from an interactive timeline displayed via a second area of the navigator interface, the navigator interface providing a single overview to facilitate navigation through care actions, a health historical record and clinical evidence generated for a patient; and a registration engine to register one or more markers indicating clinical evidence and annotations from the plurality of reference images with the current image, the registration engine to provide the one or more markers to the navigator interface to display the one or more markers on the current image, the navigator interface to display a set of available marker types corresponding to a type of each registered marker displayed on the current image, wherein the registration engine is to extract snap shot data from a plurality of historical the reference images based on the selection of a time entry on the interactive timeline displayed via a second area of the navigator interface, the registration engine to provide a synopsis and trend of clinical information associated with a selected marker type based on the snap shot data in a third area of the navigator interface, the third area overlaid on the current image in the first area upon selection of the selected marker type from the set of available marker types displayed via the navigator interface by a user, the navigator interface further providing additional information associated with a selected marker upon selection, by the user, of the selected marker on the current image, wherein the navigator interface and the registration engine are to allow the user to navigate through image and marker data over time by user selection of each of a plurality of time entries to display images and associated markers for user review, and wherein the one or more markers on the current image are visible on the current image through the third area overlaid on the current image, and wherein one or more markers corresponding to the selected marker type are highlighted on the current image when included in the synopsis.

22. The non-transitory computer-readable storage medium of claim 21, wherein the navigator interface and the registration engine are to facilitate user navigation through clinical evidence by user selection of a time entry for a study among a plurality of study entries and user selection of a marker type from among a plurality of marker types to display associated images in conjunction with markers and associated information on the images for trending and comparative data review via the navigator interface.

* * * * *